United States Patent [19]

Bailey

[11] 4,110,688
[45] Aug. 29, 1978

[54] METHOD AND APPARATUS FOR PIPE JOINT LOCATOR, COUNTER AND DISPLACEMENT CALCULATOR

[75] Inventor: John M. Bailey, Houston, Tex.

[73] Assignee: Monitoring Systems, Inc., Thibodaux, La.

[21] Appl. No.: 724,729

[22] Filed: Sep. 20, 1976

[51] Int. Cl.$^2$ .............................................. G01R 33/12
[52] U.S. Cl. ................................... 324/208; 166/65 M; 175/48; 73/151.5
[58] Field of Search ............. 324/34 R; 166/64, 65 R, 166/65 M; 175/40, 44, 45, 48; 73/151, 151.5; 235/51.32, 92. DN; 340/18 DC

[56] References Cited

U.S. PATENT DOCUMENTS

| | | | |
|---|---|---|---|
| 3,570,594 | 3/1971 | Hamilton | 166/64 |
| 3,646,808 | 3/1972 | Leonard | 175/40 |
| 3,777,560 | 12/1973 | Gnignard | 73/151.5 |
| 3,944,923 | 3/1976 | Lutheran | 324/165 |

OTHER PUBLICATIONS

Richards, R. K., Arithmetic-Operations in Digital Computers, New York (1955), pp. 136-144.

*Primary Examiner*—Robert J. Corcoran
*Attorney, Agent, or Firm*—Wilkinson, Mawhinney & Theibault

[57] ABSTRACT

The invention is a novel method and apparatus for counting pipe joints, passing through a bell nipple, going downhole and uphole by sensing, at spaced apart positions along the nipple utilizing magnetic fields, for the presence of a joint. Each sensor develops signals as the joint passes it and a logical network determines which direction the pipe joint is traveling, adds a plus count to the joint counter for joints going downhole and subtracts a minus count from the joint counter when a joint is sensed coming uphole. Another logical circuit converts the joint count to a stand count, and the negative signals from the stand count trigger an adder network to introduce a binary number to a numeric read-out display, which number is indicative of pipe displacement per stand, withdrawn from hole.

11 Claims, 7 Drawing Figures

METHOD AND APPARATUS FOR PIPE JOINT LOCATOR, COUNTER AND DISPLACEMENT CALCULATOR

PRIOR ART

The prior art reveals no such logical networks as are herein disclosed. The U.S. Pat. No. 3,646,808 to Leonard detects the amount of fluid required to replace the steel of the pipe removed from the drill hole, and automatically replaces same. U.S. Pat. No. 3,843,923 to de Vries et. al. uses a pair of Hall effect detectors for pipe joint location, and U.S. Pat. No. 3,803,797 to Abtukin et. al. checks continuity of pipe sections.

The present invention employs three magnetic pickup units at spaced apart locations to develop signals indicative of pipe joints passing the respective pickup units. The pickup units are vertically spaced apart on the bell nipple to provide directional information, because if a joint moves downhole, through the bell nipple, it will develop a signal at pickup unit 1 first, then pickup unit 2 and then pickup unit 3. However, if the joint is coming out of the hole the pickups will be tripped in the reverse order.

Pneumatic or electrical logic is utilized to add or subtract a count at the joint counter depending upon the direction of movement of the pipe. The add and subtract logic circuits are identical but inverted and hence provide both the add and subtract signals.

A three position, two way valve or switch is provided to accommodate a number of joints per stand. The switch has three inputs for a positive count and three inputs for a negative count and it is set to indicate the number of joints per stand and influence the count accordingly. If, for example, there are three joints per stand, then the switch will be set to three and after the third joint has passed the joint locator, a count will be registered on the stand counter such that the stand counter registers a count every third joint. Also the same logic subtracts a count from the stand counter when three joints have been removed from the hole.

The system also provided for a circuit for displaying mud displacement amounts. This tells how much mud must be pumped into the hole as drill pipe is withdrawn when removing pipe from the hole.

A five position valve or switch is used to set a binary number into the tenths and hundredths stages of the adders, which display, (via seven bar encoders) the numbers indicating the mud displacement. It is a five stage adder capable of counting and displaying 999.99, but the principles herein taught are applicable to other capacity adders.

The triggering inputs to the adder sections are the negative counts from the stand counter, and accordingly, the five position valve or switch is manually set to insert a binary number into the tenths and hundredths stages which represents the displacement per stand of a particular size and weight drill pipe. This number is inserted automatically each time a negative count is received. Obviously, this information could be utilized on a per joint basis, if desired.

Thus, the binary number set into the adders which represents the displacement per stand, will be added to the total each time a stand is removed from the hole. The calculated displacement number is displayed on the face of the instrument panel, as being representative of the total volume of mud which should have been pumped into the hole at any given time. This number can be compared to the actual mud pumped, or can be used to actuate an automatic fill-up system.

The invention will be better understood from a reading of the following detailed description thereof, when taken in light of the accompanying drawings wherein.

Figure 1:
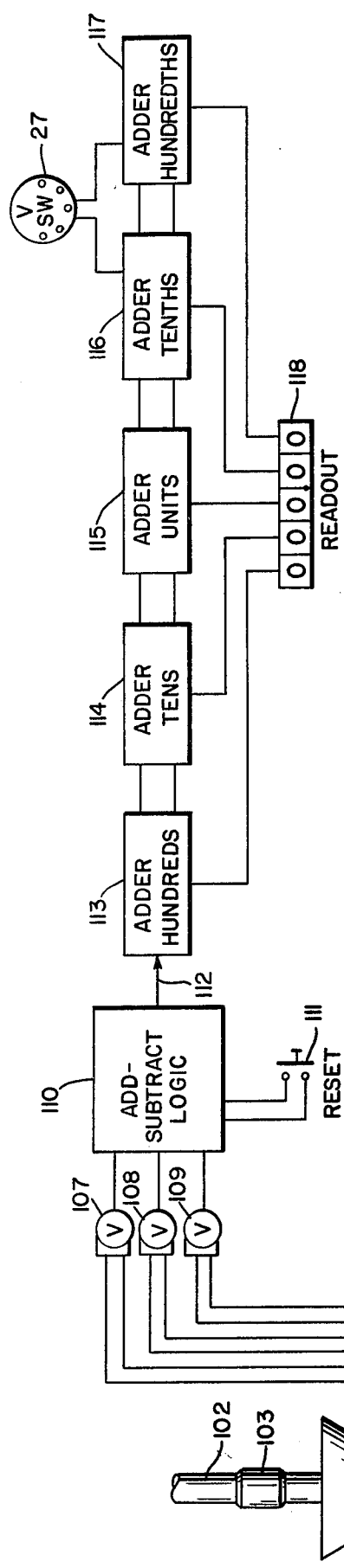
FIG. 1 is a block or schematic representation of the entire system.

The three pickup units labeled PU1, PU2 and PU3 are shown in FIG. 1 against bell nipple 101 through which pipe 102 having a joint 103 is passing.

Figure 2:
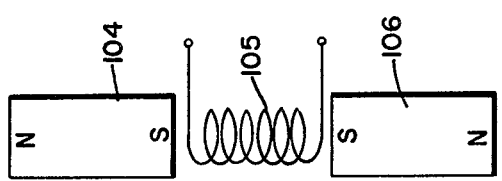
FIG. 2 shows the components for each pickup unit.

Each pickup unit is comprised of the components shown in FIG. 2, being a bar magnet 104, coil 105 and similar bar magnet 106, with the coil interposed between the magnets. It should be noted that the magnetic poles of bar magnets 104 and 106 oppose each other, i.e. South of South. This is similar to designs used in casing collar locators for downhole tools.

Figure 3:
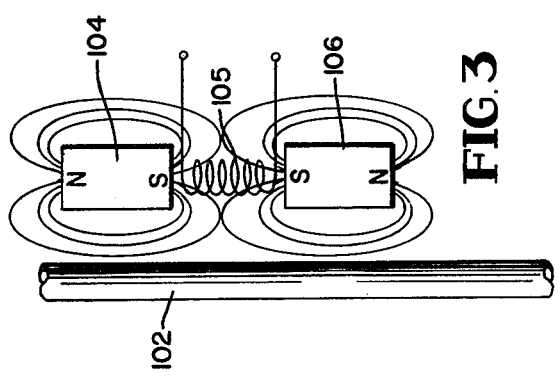
FIG. 3 depicts the flux diagram for a pickup unit in the absence of a joint.

Since the poles of the magnets oppose each other, the flux patterns from the two magnets intersect the coil in a perpendicular manner as shown in FIG. 3. The presence of a drill pipe 102 will not upset the symmetrical pattern of the flux, therefore the output from the coil 105 will be zero volts.

Figure 4:
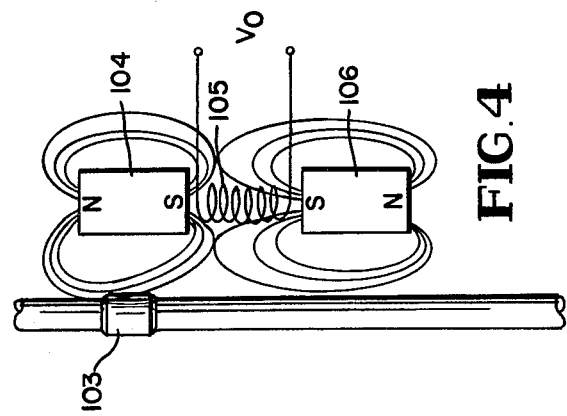
FIG. 4 shows the flux distribution pattern in the presence of a joint.

As a joint 103 approaches the locator pickup unit, the increased mass of the joint attracts the flux from the upper magnet (as seen in FIG. 4), causing the flux pattern of both magnets to move upward. The movement of the flux perpendicular to the centerline of the coil 105 causes a voltage to be generated inside the coil 105. This voltage is the signal which indicates the presence of a pipe joint.

As a joint moves downhole, through the bell nipple 101, it will trip pickup #1, then pickup #2, then pickup #3, in that order. If the joint is coming out of the hole, the pickups will be tripped in the reverse order.

In FIG. 1 a block diagram is shown of the overall system wherein the three units actuate respectively solenoid valves 107, 108 and 109. The electrical signals generated in the pickup coils 105 are transferred to solenoid valves 107, 108 and 109, serving to open these valves in sequence.

The system will be explained as employing pneumatic components, but their equivalents in electrical circuits can be substituted to make an all electric control system.

The signals from solenoid valves 107, 108 and 109 are processed in add-subtract logic counters (block 110) which includes reset buttom 111. Block 110 includes both the joint counter and stand counter of FIG. 5.

The input triggering signals to the adder circuits are the negative counts to the stand counter, which appear on lead 112 and trip the appropriate stages 113–117 of the adder circuitry for display of the displacement number on read-out panel 118.

Five position valve switch 27 puts in the correct binary number into adder stages 116 and 117 in accordance with the displacement per stand for five different pipe sizes. This binary number is added for each negative stand trigger count, such that read-out panel 118 indicates the actual mud displacement at any given time.

Figure 5:
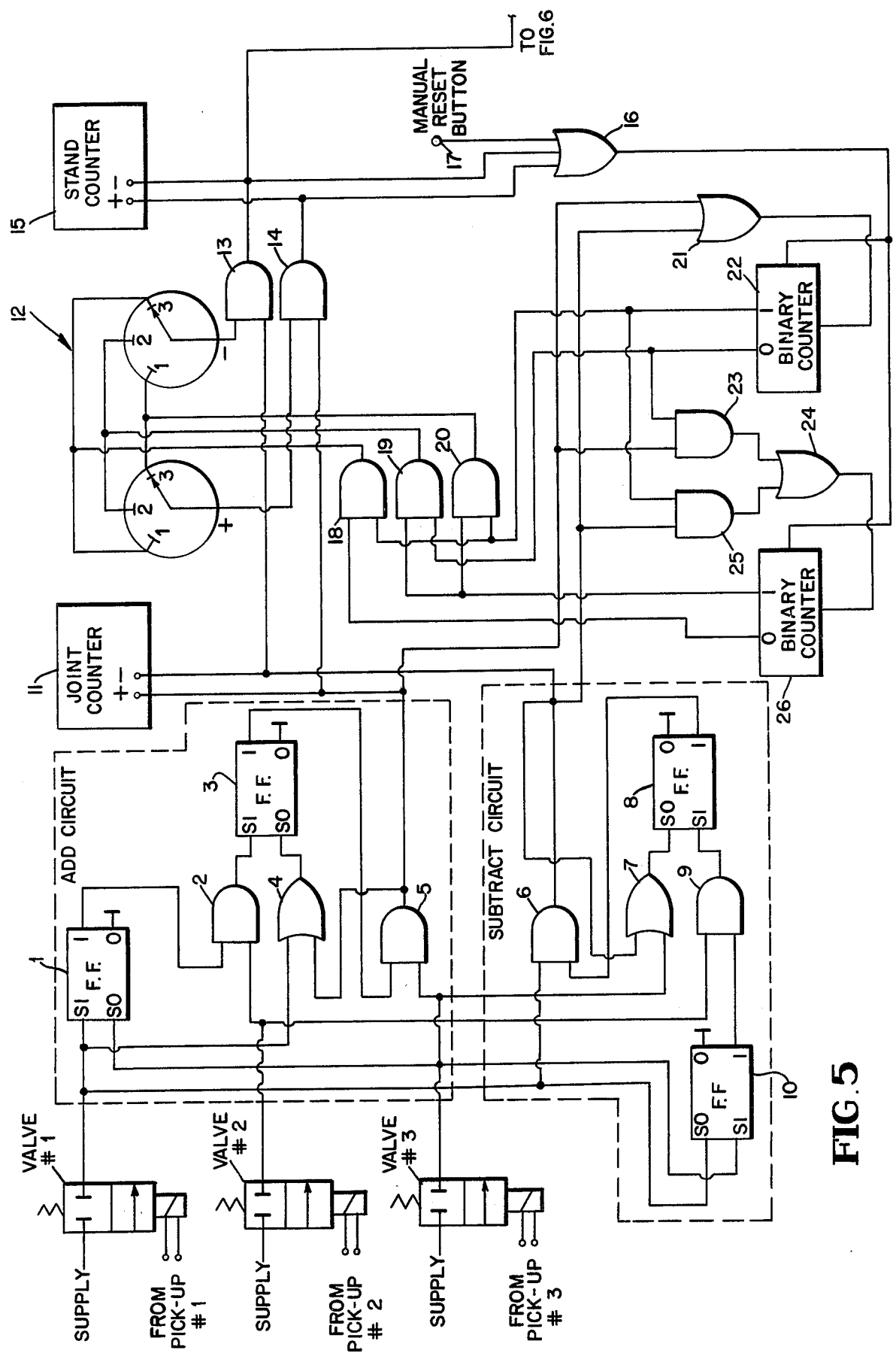
FIG. 5 shows the three pickup units setting the add-subtract logic circuitry for the joint counter, and the three position, two way valve or switch for converting joints to stands for the stand counter.

The logic diagram shown in FIG. 5 indicates the pickups actuating the three solenoid operated air valves, and the rest of logic is pneumatic. The basic logic would be the same if the system were entirely electric, however.

As a joint moves downhole, it trips pickup #1 first. This causes an output from valve #1. Look first at the upper circuit which is the add portion. Valve #1 triggers flip-flop 1 and goes through OR gate 4 to insure that flip-flop 3 is turned off. The output of flip-flop 1 goes to AND gate 2.

When valve #2 fires, its output goes to AND gate 2 and turns on flip-flop 3, which sends a signal to AND gate 5.

When valve #3 fires, its output goes to turn off flip-flop 1 and also goes to AND gate 5. The output from AND gate 5 is a pulse which is used to add one joint on the joint counter 11. The output from gate 5 also goes through OR gate 4 to turn flip-flop 3 off.

Now looking at the lower position of the counter diagram as the joint goes downhole, this portion is the subtract circuit.

Valve #1 fires first, turning off flip-flop 10, and also sending a signal to AND gate 6. Since there is no signal from flip-flop 8, there is no output from gate 6. When valve #2 fires, it sends a signal to AND gate 9, but since there is no output from flip-flop 10, gate 9 has no output, thus flip-flop 8 still has no output. When valve #3 fires, it turns on flip-flop 10, and goes through OR gate 7 to keep flip-flop 8 turned off. Thus, there is never a signal out of AND gate 6. The output from gate 6 is the signal to subtract a joint from the counter.

Therefor, as a joint moves downhole, there is a pulse out of the add circuit, and no pulse out of the subtract circuit. Since the add and subtract circuits are identical, but inverted, when a joint comes out of the hole, the subtract circuit sends a pulse to joint counter 11.

The joint counter is a count up and down counter, thus it will keep accurate count of the joints in the hole at all times.

The add and subtract pulses are also fed into a binary counter consisting of two binary counter modules 22 and 26.

These modules are connected by means of AND gates 23 and 25, and OR gate 24. This allows the binary counter to count both up and down. The outputs of the two modules connect to AND gates 18, 19 and 20. The outputs of these gates represent the counts 1, 2 and 3 respectively.

The counter will be set at zero by pressing the reset push bottom 17. Thus, the counter will always start at zero.

If the drill pipe is going into the hole, there will be an add pulse into the binary counter each time a joint passes the joint locator. The first pulse will cause an output from AND gate 18. The third pulse will cause an output from AND gate 20.

The outputs from these gates go to the ports of a 3 position, two way valve or switch 12. The switch has three inputs for a positive count, and three inputs for a negative count.

This switch is set to indicate the number of joints per stand. Assume there are three joints per stand, then the switch will be set as shown in the diagram.

After the third joint has passed the joint locator, there will be an output from AND gate 20. This output will go through switch 12, since it is set on three joints per stand, pass through AND gate 14, and register a count on the stand counter 15. The signal will also go through OR gate 16 and reset the binary counters to zero. Thus, the stand counter will register a count every third joint.

The same logic subtracts a count from the stand counter when three joints have been removed from the hole.

Figure 6:
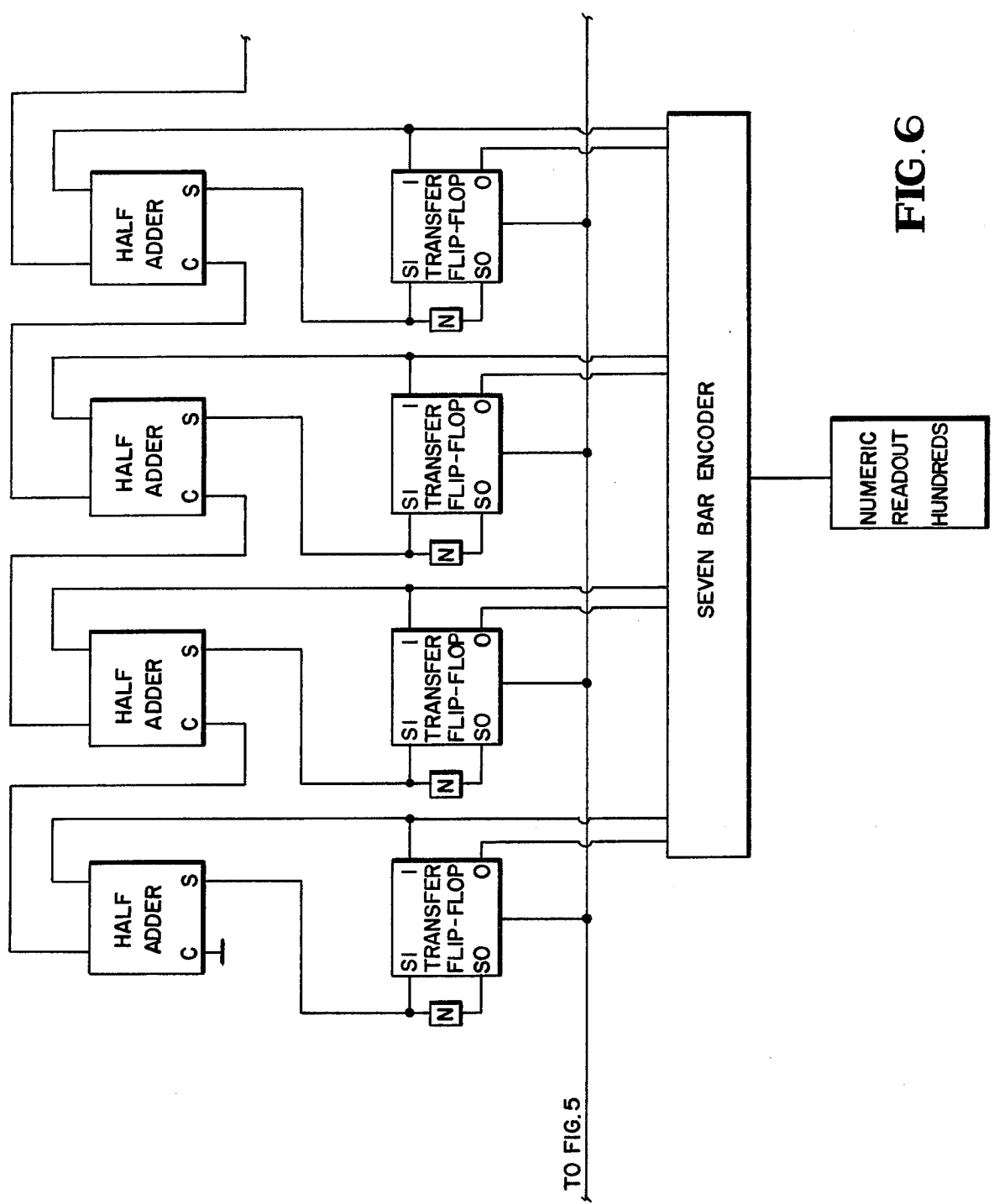
FIGS. 6 and 7 show three of five stages of the adders with the five position valve or switch for inputting the binary number representing displacement per stand or joint and, also shows the numeric read-out display panel for the displacement number calculated.
Figure 7:
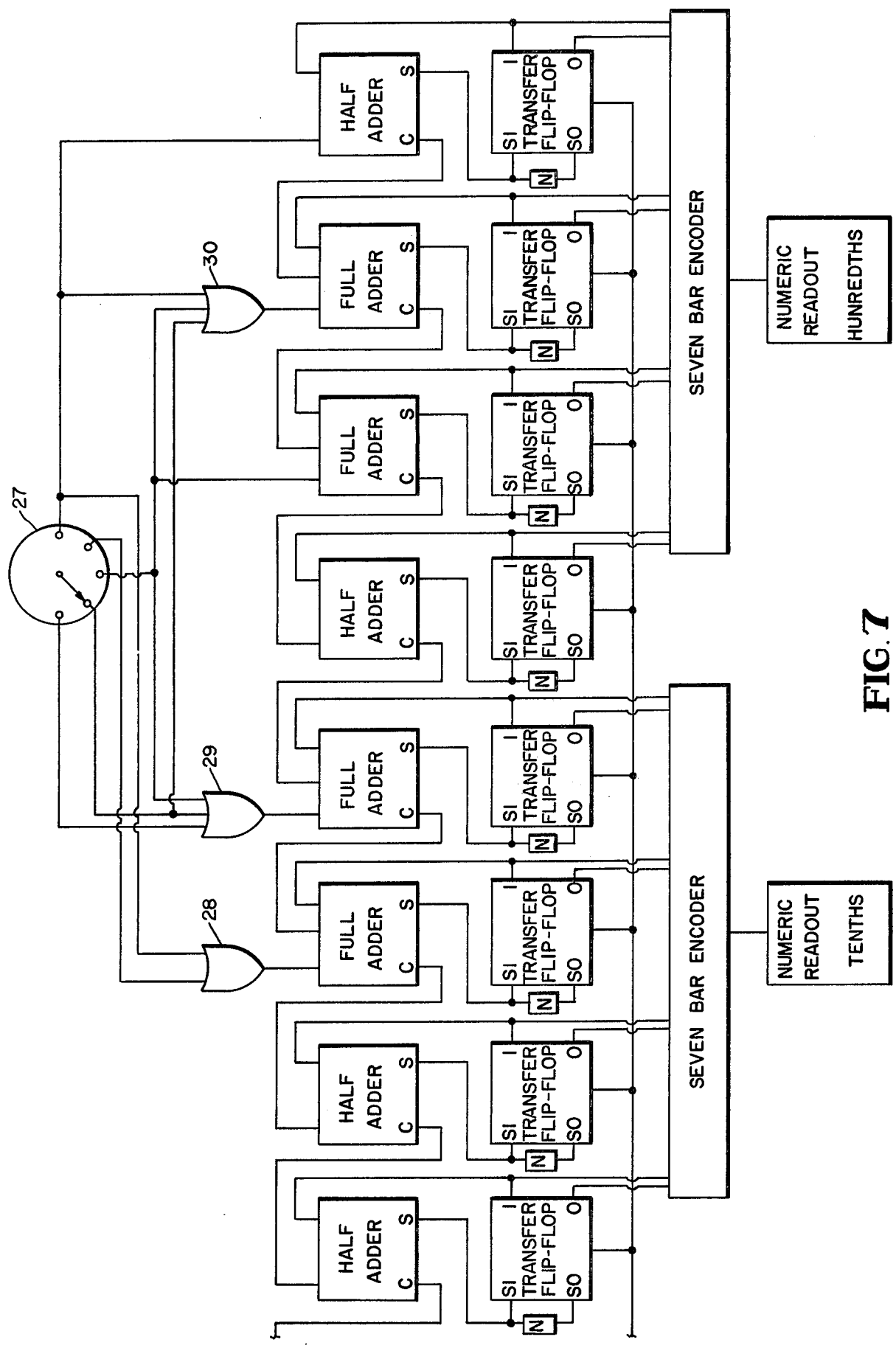

The last part of the system consists of the circuit of FIGS. 6 and 7 for displaying how much mud must be pumped into the hole as drill pipe is withdrawn when tripping the hole.

A five position valve or switch 27 is used to set a binary number into the adder system. Each position will represent the displacement per stand or per joint of a particular size and weight drill pipe.

By use of the OR gates, 28, 29, and 30, the proper binary number will be set into the adders. When the stand counter is pulsed, it will actuate the transfer flip-flops. This will transfer the number from the adders to the flip-flops.

The output from the flip-flops go to a seven bar encoder, which encodes the number and displays the number on the numeric read-outs.

The outputs from the flip-flops is also fed back into the adders, to be added to the original binary number set into the adder by the switch 27.

Thus, the original number set into the adders, which represents the displacement per stand, will be added to the total each time a stand is removed from the hole. This number will be displayed numerically on the face of the panel, and will represent the total volume of mud which should have been pumped into the hole at any given time.

This number can be compared to the actual mud pumped, or can be used to actuate an automatic fill up system.

By adding additional binary adders to the circuit, and having them triggered by the positive stand count rather than the negative count, the system can be made to calculate and display the volume of mud which should be displaced from the hole when the drill pipe is going into the hole.

If binary subtracters were added to the original system, and pulsed by the positive stand count, the system would accurately display the total mud required for the hole at all times, whether going in or coming out of the hole.

What is claimed is:

1. Apparatus for counting pipe joints passing through a drill hole bell nipple going either downhole or uphole comprising in combination:
   a. a plurality of sensor means for sensing at spaced apart positions along and externally of said bell nipple the passage of pipe joints downhole and uphole past said sensor means,
   b. logical means for logically determining the direction of pipe joint travel in circuit with and triggered by signals from said sensor means spaced along said bell nipple to develop plus signal counts for downhole going joints and minus signal counts for uphole going joints, c. joint counter means in circuit with said logical means for adding a plus signal each time a joint is sensed going downhole, and d. means in circuit with said logical means for subtracting a count from said joint counter means each time a joint is sensed coming uphole in response to said minus signal count, and e. stand counter means in circuit with said logical means for converting the joint count to a stand count using said plus and minus signal counts.

2. The apparatus of claim 1 further comprising, means including an adder network for calculating mud displacement when tripping the hole and means for displaying the displacement sum accumulated in the adder network.

3. Apparatus for calculating mud displacement as a result of removing pipes having joints from a drill hole comprising in combination:

a. a plurality of sensor means for sensing at spaced apart positions along and externally of said bell nipple the passage of pipe joints downhole and uphole past said sensor, b. means for deriving signals from said sensing means indicative of each passing joint and whether it is passing uphole or downhole by deriving a plus signal for downhole and a minus signal for uphole, c. means including an adder network selectively using the minus signals to trigger said adder network to accumulate the total volume displacement equal to the displacement of a pipe, d. said adder means employing a number indicative of incremental volumetric pipe displacement, and e. said adder means accumulating said number with each minus signal count.

4. The apparatus of claim 3 further comprising, means including a joint up and down counter for selectively using said plus and minus signals as plus and minus counts applied to the joint up and down counter to display the number of pipes within said hole;

means including an up and down stand counter for selectively using said plus and minus signals for converting the number of joints to number of stands in said hole and displaying same;

said means for selectively using said signals to trigger comprising means using only the minus counts to said stand counter; and, said number indicative of incremental volumetric pipe displacement being equal to the displacement of a stand of pipes passing uphole.

5. The apparatus of claim 3 wherein the means for deriving signals comprises:

means including solenoid valves respectively actuating said valves upon the sensing of a passing joint to develop pulses;

means including an adding circuit consisting of flip-flops, AND, and OR components to produce the downhole signals;

means including a substracting circuit which is the same as the adding circuit except inverted to produce the uphole signals; and means for displaying the net sum of said uphole and downhole signals as the count of pipe within said hole.

6. The apparatus of claim 4 further comprising, inserting means including a multi-position valve switch for determining the number equal to the displacement of a stand of pipes and for inserting it into the adder network by selectively setting the switch to the position corresponding to the displacement of a stand of particular pipe and joint being removed.

7. The method of counting pipe joints passing through a drill hole bell nipple going either downhole or uphole comprising in combination:

a. sensing at spaced apart positions along and externally of said bell nipple the passage of pipe joints downhole and uphole past said sensor means, b. logically determining the direction of pipe joint travel by means in circuit with and triggered by the sensed signals spaced along said bell nipple to develop plus signal counts for downhole going joints and minus signal counts for uphole going joints, c. adding a plus signal to a joint count each time a joint is sensed going downhole, and d. subtracting a count from said joint count each time a joint is sensed coming uphole in response to said minus signal count, and e. converting the joint count to a stand count using said plus and minus signal counts.

8. The method of calculating mud displacement as a result of removing pipes having joints from a drill hole comprising in combination:

a. sensing at spaced apart locations along and externally of said bell nipple the passage of pipe joints downhole and uphole past said sensor means, b. deriving signals from said sensing means indicative of each passing joint and whether it is passing uphole or downhole by deriving a plus signal for downhole and a minus signal for uphole, c. adding selectively using the minus signals to trigger said adding to accumulate the total volume displacement equal to the displacement of a pipe by employing a number indicative of incremental volumetric pipe displacement, and accumulating said number with each minus signal count.

9. The method of claim 8 further comprising, displaying the displacement sum accumulated in the adding step.

10. The method of claim 8 wherein the step of deriving signals comprises:

a. respectively actuating solenoid valves upon the sensing of a joint passing the sensing locations to develop pulses, b. applying said pulses to an adder network of flip-flops, AND, and OR components to produce the uphole signal, c. applying said pulses to a subtracting circuit which is the same as the adding network except inverted to produce the uphole signals, d. and displaying the net sum of said uphole and downhole signals as the count of pipe within said hole.

11. The method of claim 8 wherein said number indicative of incremental volumetric pipe displacement is inserted into the adder network by a multi-position valve switch selectively set to the position corresponding to the displacement of a stand of particular pipe and joint being removed.

* * * * *